United States Patent [19]

Schmittou

[11] Patent Number: 5,141,855
[45] Date of Patent: Aug. 25, 1992

[54] SIGNAL AMPLIFYING COBALT (III) REDOX REAGENTS AND METHODS FOR THE DETERMINATION OF ANALYTES IN AQUEOUS FLUIDS

[75] Inventor: Eric R. Schmittou, Rochester, N.Y.

[73] Assignee: Eastman Kodak Company, Rochester, N.Y.

[21] Appl. No.: 890,051

[22] Filed: Jul. 28, 1986

[51] Int. Cl.⁵ ............... G01N 31/22; G01N 33/52; G01N 33/50; C12Q 1/04

[52] U.S. Cl. .................. 435/34; 435/4; 435/25; 435/26; 435/28; 435/29; 435/30; 436/84; 436/169; 436/170; 436/904; 422/55; 422/56; 422/57; 430/223; 430/224; 430/225; 556/138; 556/140; 556/146; 556/148

[58] Field of Search .............. 435/4, 25, 26, 28, 29, 435/30, 34; 436/84, 164, 169, 170, 903, 904; 422/55-57; 430/223-225; 260/396 R, 397.6; 556/138, 140, 146, 148

[56] References Cited

U.S. PATENT DOCUMENTS

| | | |
|---|---|---|
| 3,331,752 | 7/1967 | Struck, Jr. et al. ............ 195/103.5 |
| 3,928,139 | 12/1975 | Dorn .............................. 435/34 |
| 4,042,335 | 8/1977 | Clément ......................... 422/56 |
| 4,045,221 | 8/1977 | Dominh ......................... 430/235 X |
| 4,045,221 | 8/1977 | DoMinh ......................... 96/29 R |
| 4,144,306 | 3/1979 | Figueras ........................ 436/170 X |
| 4,195,998 | 4/1980 | Adin et al. ..................... 430/156 |
| 4,258,001 | 3/1981 | Pierce et al. ................... 422/56 |
| 4,376,820 | 3/1983 | Giannini et al. ................ 435/4 |
| 4,419,435 | 12/1983 | Reczek et al. .................. 430/223 |
| 4,421,846 | 12/1983 | Ikeuchi et al. .................. 430/559 |
| 4,610,961 | 9/1986 | Guardino et al. ............... 435/34 |
| 4,701,420 | 10/1987 | Thunberg et al. .............. 422/56 X |
| 4,746,607 | 5/1988 | Mura et al. .................... 435/29 X |
| 4,755,472 | 7/1988 | Ismail et al. ................... 435/28 |

FOREIGN PATENT DOCUMENTS

| | | | |
|---|---|---|---|
| 0255087 | 2/1988 | European Pat. Off. | 435/4 |
| 2195559 | 8/1987 | Japan | 435/4 |

*Primary Examiner*—Esther L. Kepplinger
*Assistant Examiner*—Carol A. Spiegel
*Attorney, Agent, or Firm*—Doreen M. Wells

[57] ABSTRACT

Reagents and methods for the determination of analytes are disclosed, using water soluble cobalt(III) complexes and metallizable dyes to form cobalt(III) complexes of the metallizable dyes. Analytes which can be determined include enzymes, cells and biological reductants, such as NADH, NADPH and ascorbate. Amplification is provided since one equivalent of the analyte provides more than one equivalent of the detectable species.

29 Claims, No Drawings

SIGNAL AMPLIFYING COBALT (III) REDOX REAGENTS AND METHODS FOR THE DETERMINATION OF ANALYTES IN AQUEOUS FLUIDS

FIELD OF THE INVENTION

The present invention relates to methods, compositions and elements for the determination of analytes in aqueous fluids. In preferred embodiments, the aqueous fluid is a biological fluid or a fluid that is derived from a biological fluid.

BACKGROUND OF THE INVENTION

Chemical analysis of aqueous fluids, such as effluent streams, and biological fluids are important for health maintenance and diagnostic care. Frequently, the material to be determined, the analyte, is present in the fluids in very small amounts and conventional analytical methods lack the sensitivity to accurately measure such small quantities.

Many biologically significant substances can be quantifiably determined using a reaction or sequence of reactions that produce a reductant. For example, nicotinamide adenine dinucleotide, reduced form, otherwise known as NADH, is commonly produced in these reactions. Another common reductant is the corresponding phosphate, otherwise known as NADPH. Conventional assay methods usually monitor NADH or NADPH by directly measuring the change in the solution absorbance when these species are produced. These conventional assays suffer from the drawbacks that they are relatively insensitive and are limited to measurements at about 340 nm, where many interferents also have absorptions.

To improve the sensitivity of these assays, these species are used to reduce a tetrazolium salt to yield a formazan dye. However, formazan dyes themselves have low extinction coefficients and thus, the sensitivity is not sufficiently improved by this method.

It has also been suggested in U.S. Pat. No. 3,331,752 to reduce a ferric ion chelate with the NADH to produce a ferrous ion chelate with different absorption characteristics than the ferric ion chelate. This method also has less than the desired sensitivity since there is no amplification step involved.

In copending commonly assigned U.S. Pat. No. 4,701,420, issued Oct. 20, 1987, entitled ANALYTICAL COMPOSITIONS, ELEMENTS AND METHODS UTILIZING REDUCTION OF FERRIC ION CHELATES TO FORM DETECTABLE DYES, there is disclosed an improved method involving ferric ion chelates. While this method involves advantages over that disclosed in the '752 patent, it still does not provide an amplification step and therefore does not have the required sensitivity.

The problem to be solved, therefore, is to provide methods and reagent compositions with improved sensitivity. This is accomplished by providing an amplification step. Amplification occurs when one equivalent of an analyte gives more than one equivalent of detectable species.

SUMMARY OF THE INVENTION

The assay of the present invention provides the desired amplification using a method for the detection of an analyte in an aqueous sample comprising the steps of:

(a) contacting said sample with reagents which effect, in the presence of a reductantpositive sample, a sequence of reactions wherein:
  (1) a water soluble cobalt(III) complex is reduced to a water soluble cobalt(II) complex by said reductant.
  (2) the cobalt(II) complex reacts with a water soluble metallizable dye to form a cobalt(II) complex of the metallizable dye and
  (3) the cobalt(II) complex of the metallizable dye reacts with the cobalt(III) complex to produce a cobalt(III) complex of the metallizable dye and the cobalt(II) complex, and (b) detecting the cobalt(III) complex of the metallizable dye.

In another aspect of the present invention there is provided a reagent composition for carrying out the above method. The reagent composition for the detection of an analyte in an aqueous sample comprises:

(1) a water soluble cobalt(III) complex which is capable of being reduced to a water soluble cobalt(II) complex by said analyte and, (2) a water soluble dye which is capable of being metallized by said cobalt(II) complex to form a water soluble cobalt(II) complex of the metallizable dye, wherein said cobalt(II) complex of the metallizable dye is capable of reacting with said cobalt(III) complex to produce a cobalt(III) complex of the metallizable dye and the cobalt(II) complex.

DETAILED DESCRIPTION OF THE INVENTION

The present invention provides amplification because of the regeneration of the cobalt(II) complex. Thus, more than one equivalent of the cobalt(III) complex of the metallizable dye is produced for each equivalent of the analyte that reacts. An equivalent can be defined as that amount of an analyte or reactant that accepts or gives up 1 mole of electrons. The reactions can be written as follows:

1) cobalt(III) complex + reductant → cobalt(II) complex
2) cobalt(II) complex + dye → cobalt(II)-dye complex
3) cobalt(II)-dye complex + cobalt(III) complex → cobalt(III)-dye complex + cobalt(II) complex The last two reactions can be represented by the following:

4) dye + cobalt(III) complex → cobalt(III)-dye complex

The present invention is made possible by several inherent features of the materials involved. For example, the cobalt(III) complex of the metallizable dye can be detected in the presence of the unmetallized dye because the absorption spectrum of the cobalt(III)-dye complex is significantly different from the spectrum of the unmetallized dye. A shift in the wavelength of maximum absorption of the dye occurs when the dye becomes metallized. This shift is usually greater than 50 nm. Thus, the presence of the metallized dye is easily followed at its characteristic wavelength. Also, the cobalt(III) complex undergoes reactions that change its ligands much more slowly than does the cobalt(II) complex. This means that the dye cannot react directly with the cobalt(III) complex but requires that the cobalt(III) complex first be reduced to the cobalt(II) complex. Thus, reaction 4) does not occur spontaneously at a significant rate. Instead, reaction 4) proceeds because it is being catalyzed by the cobalt(II) species present in the system.

This invention is useful for the determination of any analyte that is either itself a reductant or is capable of producing a reductant that can reduce the cobalt(III) complex to a cobalt(II) complex via a single reaction or a sequence of reactions.

The various analytes include living cells (e.g. bacteria, white blood cells, yeast, fungi, etc.), enzymes (e.g. lipase, glucose oxidase, lactate oxidase, α-glycerophosphate oxidase, lactate dehydrogenase, pyruvate dehydrogenase, glucose-6-phosphate dehydrogenase, alanine aminotransferase, aspartate aminotransferase) and other analytes that produce NADH or FADH through a reaction sequence, biological or chemical reductants (e.g. ascorbates, cysteine, glutathione, thioredoxin, etc.), metabollizable substances (e.g. glucose, lactic acid, triglycerides, cholesterol, etc.) and immunoreactants (e.g. antigens, antibodies, haptens, etc.).

This invention is particularly useful in the determination of living cells. Some cells require an electron transfer agent (ETA) to effect efficient reduction of the cobalt(III) complex. An ETA is a mobile species that can readily transfer electrons from the cells to the cobalt(III) complex. This can be called an indirect process as opposed to a direct reduction of the cobalt(III) complex by an analyte, e.g. ascorbate. The presence of an ETA may also provide more efficient reduction in the determinations of non-living analytes.

An imaging system based on cobalt(III) chemistry is known in the photographic art. However, no use has been made of this chemistry for the determination of analytes in aqueous fluids, particularly biological analytes. In fact, the materials, in particular, the metallizable dyes, that are used in the references disclosing the photographic uses of this chemistry are typically not water soluble and would therefore not be useful in the present invention. Typical references which disclose photographic uses of cobalt(III) chemistry include U.S. Pat. Nos. 4,421,846; 4,045,221; and 4,195,998.

For the purposes of the present invention, it is necessary that the reagents be water soluble. By water soluble it is meant that the compound is capable of dissolving in the reaction solution so as to form a solution of the compound of at least about $1 \times 10^{-5}$ Molar. The reaction solution is the solution which contains all of the reagents and the sample. In solution assays, the reaction solution contains the sample mixed with an aqueous solution of reagents. In dry assays, the reagents are readily dispersed directly in the element.

In the present invention, a cobalt(III) complex is used. Cobalt(III) is a trivalent metal that typically has a coordination number of six. An extremely wide variety of ligands are known to coordinate to cobalt(III). If the ligands are selected so that they contain a negative charge, a valence can be satisfied by the ligand. Conversely, if the ligand is electrically neutral, the valence must be satisfied by a non-coordinated counter-ion and a salt is formed. For use in the present invention, water soluble complexes are required. The cobalt(III) complex salts, being more water soluble, are preferred.

Useful neutral ligands for forming Co(III) complexes include: ammonia; aliphatic amines, such as ethylenediamine, propylenediamine, diethylenetriamine; substituted or unsubstituted aromatic amines, such as aniline, 2-aminoethylaniline, 2,2'-bisaniline; substituted or unsubstituted heterocyclic amines, such as pyridine, 2,2'-bipyridine, 2-(aminomethyl)pyridine, 4,4'-dimethyl-2,2'-bipyridine, 2,2',2''-terpyridine, morpholine, pyrimidine, pyridazine, 2,2'-bipyrazine quinoline, isoquinoline, acridine, thiazole, imidazole, triazine, 1,10-phenanthroline, 5-nitrophenanthroline, 2,2'-bipyrimidine, 2,2'-diimidazole; and oxygen donor ligands, e.g. amides such as N,N-dimethylformamide and water. Any anion can be used as the counter ion. For convenience, halide ions are preferred such as chloride, bromide and iodide. Other useful counter anions include, for example, azide, thiocyanate, tetrafluoroborate, nitrate, perchlorate, hexafluorophosphate, sulfate, carbonate, sulfonate and carboxylate ions.

Anionic ligands may also coordinate with cobalt(III) provided the charge on cobalt(III) is not completely neutralized by the ligands, so that the complex is a salt and therefore water soluble. Useful anionic ligands include halide, i.e., chloride, bromide, iodide or fluoride, azide, thiocyanate, nitrite, carbonate, carboxylate, sulfonate, oxalate and 2,4-pentanedionate ions.

The reactions of the present invention, described above, are redox reactions and it is useful to describe the reactants in terms of their redox potentials, $E^o$. The method for the determination of the $E^o$ values reported in the tables below is a standard method which is described in detail in a section just preceding the examples. The rate constants in the tables below were determined spectrophotometrically by measuring the rate of catalyzed reaction 4) under standard conditions. The rate constants are a measure of the relative speed of amplification.

Cobalt(III) complexes that are useful in the present invention have a potential greater than $-350$ mV, preferably greater than about $-100$ mV. If the potential is more negative than about $-100$ mV, the rate of cobalt(II) complex formation, reaction 3), may be too slow to be practical for some purposes.

Specific preferred cobalt(III) complexes and their potentials and rate constants are listed below in Table I:

In the table below, "en" stands for ethylenediamine. Rate constants are given in $1\ mol^{-1} sec^{-1}$ and $E^o$ values are given in mV versus the normal hydrogen electrode (NHE).

TABLE I

|  | Cobalt (III) Complex | Rate Constant$^a$ | $E^o$ |
|---|---|---|---|
| C-1 | [Coen$_2$(2,2'-bipyridine)]Cl$_3$ | 5.0 | $-48$ |
| C-2 | [Coen$_2$(1,10-phenanthroline)]Cl$_3$ | 4.2 | $-44$ |
| C-3 | [Co[2-(aminomethyl)pyridine)$_3$]Br$_3$ | 7.5 | $-19$ |
| C-4 | [Co(NH$_3$)$_5$HCON(CH$_3$)$_2$](BF$_4$)$_3$ | 0.9$^b$ | NM |
| C-5 | [Co(NH$_3$)$_5$pyridine]I$_3$ | 0.7$^b$ | NM |
| C-6 | [Coen$_2$(2,2'-bipyrimidine)]Cl$_3$ | 42.3 | 140 |
| C-7 | [Coen$_2$(4,4'-dimethyl-2,2'-bipyridine)]Cl$_3$ | 4.8 | $-64$ |
| C-8 | [Coen$_2$(5,6-dimethyl-1,10-phenanthroline)]Cl$_3$ | 2.9 | $-109$ |
| C-9 | [Coen$_2$(4,7-dimethyl-1,10-phenanthroline)]Cl$_3$ | 2.0 | $-102$ |
| C-10 | [Coen$_2$(5-nitro-1,10-phenanthroline)]Cl$_3$ | 87.5 | $+25$ |
| C-11 | [Coen$_3$]Cl$_3$ | 0.06 | $-303$ |
| C-12 | [Co(NH$_3$)$_6$]Cl$_3$ | 0.1 | NM |
| C-13 | [Coen(2,2'-bipyridine)$_2$]Cl$_3$ | 260 | 105 |
| C-14 | [Co(2,2'-bipyridine)$_3$](BF$_4$)$_3$ | 1250 | 330 |
| C-15 | [Co(NH$_3$)$_5$OH$_2$](BF$_4$)$_3$ | 0.2$^b$ | NM |

$^a$ = At 25° C., unless specified otherwise.
$^b$ = At 37° C.
NM = Not measureable.

The other component that is used in the method and composition of the present invention is a water soluble metallizable dye. A very wide variety of dyes that are capable of coordinating with a cobalt(II) and (III) ion are useful. According to the present invention, the dyes must be water soluble. Many of the specific dyes listed in the references below are not water soluble but can be easily made so by the incorporation of a suitable solubilizing group in the dye molecule by conventional methods. Conventional solubilizing groups such as carboxylic acid, sulfonic acid and sulfate groups are useful.

The potential of importance for the dye is for the reaction: Co(II)-dye complex⇌Co(III)-dye complex +e−. In the data which follows, this potential was measured by forming a cobalt(II)-dye complex in situ by adding an appropriate amount of cobalt(II) chloride to a dye solution. While the cobalt(II) did not come from the reduction of a cobalt(III) complex, the method is an accurate indication of which dyes will be useful in the process since cobalt(II) complexes are kinetically more labile than the cobalt(III) complexes and readily form Co(II)-dye complexes. Thus, the use of cobalt(II) chloride is a good simulation of the reductant-generated cobalt(II) since any ligands present would only be loosely bound to the cobalt(II) and could be easily displaced by the appropriate metallizable dye.

The dyes that are preferred in the present invention form Co(II)-complexes which have a potential of less than about 450 mV, preferably between about 150 and 350 mV. If dissolved molecular oxygen is present, the cobalt(II)-dye complex in reaction 3) above could be oxidized by the oxygen as well as by the Co(III) complex if the potential is less than about 150 mV. If the potential is above about 350 mV, the reaction will proceed at too slow a rate to be practical for some purposes.

Preferred dyes are also tridentate ligands for cobalt. Tridentate ligands form more stable complexes and therefore can more easily displace ligands from the cobalt(II) complex.

With these criteria in mind, useful dyes and dye classes are disclosed in U.S. Pat. Nos. 4,396,546; 4,273,708; 4,272,434; 4,024,993; 4,147,544 and 4,419,435.

Azo, hydrazone and formazan dyes are useful in the practice of this invention. Azo dyes, such as azonaphthol, azophenol and azobenzoic acid dyes are preferred.

Particularly preferred azo dyes have the following generic structure:

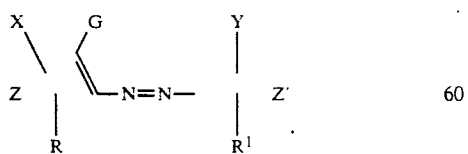

wherein

Z represents the atoms necessary to complete a substituted or unsubstituted aromatic carbocyclic or heterocyclic nucleus having at least one ring of 5 to 7 atoms, such as phenyl, pyridyl, naphthyl, pyrazolyl, indolyl, etc.;

Z' is a substituted or unsubstituted aromatic carbocyclic or heterocyclic nucleus having at least one ring of 5 to 7 atoms (e.g. the same nuclei as described above for Z), in addition, the Z' having, in a position adjacent to the point of attachment to the azo linkage, either (a) a nitrogen atom in the ring of the nucleus which acts as a chelating site, or (b) a carbon atom in the ring of the nucleus having attached thereto a nitrogen atom, which acts as a chelating site, such as a sulfamoyl or amine group;

G is a metal chelating group (any group which will donate a pair of electrons to a metal ion) or a salt thereof (e.g. an alkali metal salt, a quaternary ammonium salt, etc.) or a hydrolyzable precursor thereof (e.g. a hydrolyzable acyl or ester group), hydroxy; amino; carboxy; sulfamoyl; a hydrolyzable group having the formula $-OCOR^2$, $-OCOOR^2$, $-CON(R^2)_2$ or $COOR^2$, wherein $R^2$ is an alkyl group having 1 to about 4 carbon atoms, such as methyl, ethyl, isopropyl, etc. or an aryl group of 6 to 8 carbon atoms, such as phenyl;

R and $R^1$ independently represent hydrogen, or one or more substituents, e.g. substituted or unsubstituted alkyl of 1 to 10 carbon atoms, such as methyl, ethyl, isopropyl, carboxymethyl, carboxyethyl, etc., substituted or unsubstituted alkoxy of 1 to 10 carbon atoms, such as methoxy, ethoxy, carbomethoxy, carboethoxy, etc., nitro, halo, such as chloro, bromo or fluoro, hydroxy, substituted or unsubstituted amino ($-NR^3R^4$, wherein $R^3$ and $R^4$ are independently hydrogen, alkyl of 1 to 10 carbon atoms, such as methyl, ethyl, etc., phenyl, or $R^3$ and $R^4$ taken together can form a heterocyclic ring of 5 to 10 atoms, such as morpholino, piperidino, etc.), substituted or unsubstituted sulfamoyl ($-SO_2NR^5R^6$, wherein $R^5$ and $R^6$ are the same as described for $R^3$ and $R^4$ above); and X and Y independently represent a group mentioned for R and $R^1$ and at least one of X and Y is a solubilizing group, e.g. carboxylic acid ($-COOH$), sulfonic acid ($-SO_3H$), alkylsulfonic acid of 1 to 5 carbon atoms, such as ethanesulfonic acid ($-CH_2CH_2SO_3H$), an alkanesulfonic acid of 1 to 5 carbon atoms derived from a sulfamoyl group, such as $-SO_2NHCH_2CH_2SO_3H$ or $-SO_2N(CH_2CH_2SO_3H)_2$, sulfate ($-OSO_3H$), sulfinic acid ($-SO_2H$) or salts thereof.

Useful dyes are listed below in the following tables. Rate constants are given in L mol$^{-1}$ sec$^{-1}$ at 25° C. and E° values are given in mV versus the normal hydrogen electrode (NHE).

TABLE II-A

Azo Dyes Derived From α-Naphthol

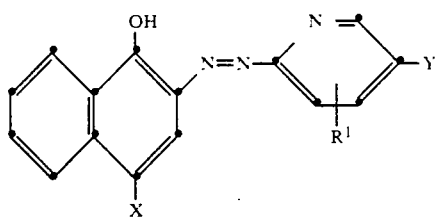

| | X | Y | $R^1$ | Rate Constant | $E^o$ (Co(II)-complex) |
|---|---|---|---|---|---|
| D-1 | $SO_2N(CH_2CH_2OSO_3^-NH_4^+)_2$ | H | H | 4.7 | 256 |
| D-2 | $SO_3^-NH_4^+$ | H | H | 5.1 | 241 |
| D-3 | $SO_3^-NH_4^+$ | H | 3-$CH_3$ | 20.7 | 188 |
| D-4 | $SO_3^-(NH(CH_2CH_3)_3)^+$ | H | H | 5.1 | 241 |
| D-5 | $SO_3^-(NH(CH_2CH_3)_3)^+$ | H | 3-$CH_3$ | 20.7 | 188 |
| D-6 | $SO_3^-NH_4^+$ | $-COO^-NH_4^+$ | H | 14.6 | 227 |
| D-7 | $SO_3^-NH_4^+$ | $-SO_3^-NH_4^+$ | 3-$CH_3$ | 5.8 | 256 |
| D-8 | $SO_3^-NH_4^+$ | $-CH_3$ | H | 7.8 | 216 |
| D-9 | $SO_3^-NH_4^+$ | $-COO^-NH_4^+$ | 3-$OCH_3$ | 18.7 | 204 |
| D-10 | N-morpholino | $-SO_3^-NH_4^+$ | 3-$CH_3$ | 26 | 67 |
| D-11 | N-morpholino | $SO_2NHCH_2CH_2SO_3H$ | 3-Cl | 0.5 | NM |
| D-12 | $CH_3-CH(O-)-CO_2^-NH_4^+$ | H | H | 78 | 86 |
| D-13 | $CH_3CH(O-)-CO_2H$ | H | 3-Cl | 23 | 192 |
| D-14 | $CH_3CH(O-)-CO_2H$ | $-SO_2NH_2$ | 3-$OCH_3$ | 4.7 | 310 |
| D-15 | $CH_3CH(O-)-CO_2H$ | $-NO_2$ | H | 0.5 | 370 |
| D-16 | $SO_3^-NH_4^+$ | [pyrimidine-OCH$_3$ substituent] | | 0.1 | 426 |
| D-17 | $SO_3^-NH_4^+$ | $-SO_2NH_2$ | 3-$OCH_3$ | 0.2 | 392 |
| D-18 | $SO_3^-NH_4^+$ | $-SO_3^-NH_4^+$ | $OCH_3$ | 2.1 | 278 |

TABLE II-A-continued

Azo Dyes Derived From α-Naphthol

[Structure: α-naphthol with OH at position 1, X at position 4, and azo group N=N linked to a heterocyclic ring bearing N=, R¹, and Y substituents]

| | X | Y | R¹ | Rate Constant | E° (Co(II)-complex) |
|---|---|---|---|---|---|
| D-19 | CH₃CH—COO⁻NH₄⁺ with O above (ketone) | —COO⁻NH₄⁻ | Cl | 54.5 | 170 |

NM = Not measureable.

TABLE II-B

Azo Dyes Derived from β-Naphthol

| | Structure | Rate Constant | E° (Co(II)-complex) |
|---|---|---|---|
| D-20 | β-naphthol with SO₃⁻NH₄⁻ groups at 6 and 3 positions, OH, and azo-linked heterocycle | 48 | NM |
| D-21 | β-naphthol with COOH, OH, azo-linked heterocycle | 480 | 253 |
| D-22 | β-naphthol with NaO₃S, OH, azo-linked heterocycle | 6.6 | 240 |
| D-23 | β-naphthol with COOH, OH, azo-linked heterocycle bearing two CH₃ groups | 95 | 262 |

NM = Not measureable

TABLE III

Azophenol Dyes

| | | Rate Constant | E° (Co(II)-complex) |
|---|---|---|---|
| D-24 | [structure: 2-OH, 4-OCH₃, 5-OCH₃ phenyl-N=N-pyridine with CH₃ and SO₃⁻Na⁺] | 10.8 | 146 |
| D-25 | [structure: 2-OH, 4-OCH₃, 5-OCH₃ phenyl-N=N-pyridine with Cl and SO₂NHCH₂CH₂SO₃⁻Na⁺] | 0.6 | 291 |

TABLE IV

Hydrazone Dyes

| | | Rate Constant | E° (Co(II)-complex) |
|---|---|---|---|
| D-26 | [structure: 6-methylpyridine-CH=N-NH-pyridine with CH₃ and SO₃H] | 43 | −50 |
| D-27 | [structure: methylpyridine-CH=N-NH-pyridine with Cl and SO₂NHCH₂CH₂SO₃H] | 0.6 | 128 |

TABLE V

Azobenzoic Acid Dyes

| | | Rate Constant | E° (Co(II)-complex) |
|---|---|---|---|
| D-28 | [structure: 2-COOH, 5-(HO₃SCH₂NH), 4-CH₃ phenyl-N=N-pyrazole (NH)] | 16.7 | NM |

NM = Not measureable.

TABLE VI

| Formazan Dyes | Rate Constant | E⁰ (Co(II)-complex) |
|---|---|---|
| D-29 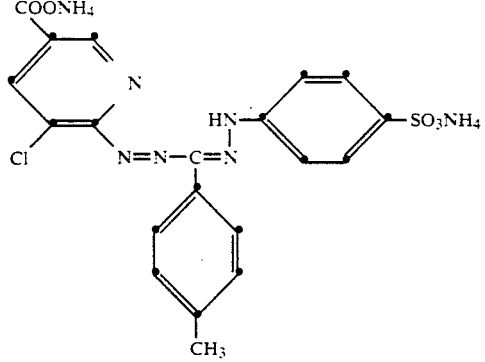 | 12 | NM |

NM = Not measureable.

The preferred dyes are D-3, D-6 and D-7 whose common names are 2-[(3-methyl-2-pyridyl)azo]-1-naphthol-4-sulfonic acid, monoammonium salt; 2-[(5-carboxy-2-pyridyl)azo]-1-naphthol-4-sulfonic acid, diammonium salt; and 2-[(3-methyl-5-sulfo-2-pyridyl)azo]-1-naphthol-4-sulfonic acid, diammonium salt.

The composition of this invention optionally, but preferably, includes an electron transfer agent (identified herein as ETA) which can transfer electrons from the reductant to the cobalt(III) complex. In general, it is desirable that the ETA has a potential which is more positive than that of the reductant and less positive than that of the cobalt(III) complex.

ETA compounds useful in the practice of this invention include phenazine methosulfate, phenazine ethosulfate, and similar compounds, and substituted benzoquinones and naphthoquinones such as those described in copending and commonly assigned U.S. Pat. No. 4,746,607, issued May 24, 1988, filed Feb. 7, 1985 by A. J. Mura et al and entitled USE OF SUBSTITUTED QUINONE ELECTRON TRANSFER AGENTS IN ANALYTICAL DETERMINATIONS. Combinations of different ETA compounds can be used if desired. The preferred ETAs are trimethyl-1,4-benzoquinone, 4,5-dimethoxy-1,2-benzoquinone and 2,3-dimethoxy-5-methyl-1,4-benzoquinone.

The analytical composition of this invention can be used in both solution and dry element assays to detect or quantify an analyte. The analytical composition can be prepared for use in a solution assay by mixing the cobalt(III) complex, the metallizable dye, and optionally the ETA, in water. The details of preparing a representative analytical composition are given in Example 1 below. Other optional components can also be included in the compositions, including buffers, surfactants, interactive compositions (described below), etc.

The detection of living cells, and particularly of bacterial cells, is often carried out in the presence of a nutrient for those cells although its presence is not essential. Any nutrient medium can be used which contains useful carbon, and optionally nitrogen, sources. Suitable nutrient media having proper components and pH are well known in the art. Particularly useful nutrients are glucose or tryptose alone or in combination.

When the compositions of this invention are used in solution assays, generally the cobalt (III) complex is present in a concentration of up to about 20 mg/ml in the reaction solution, and preferably from about 0.2 to about 2.0 mg/ml of solution. When used, the ETA is present in an amount up to 0.3, and preferably from about $5 \times 10^{-4}$ to about 0.05 mg/ml. The metallizable dye is generally present in an amount up to 5, and preferably from about 0.01 to about 0.5 mg/ml. When NADH or NADPH are determined in response to the presence of another analyte in the assayed sample, the corresponding oxidized form, NAD or NADP, is generally added to the solution in an amount up to about 10 mg/ml. The amounts of the other optional composition components (e.g. buffer, surfactant, substrate, etc.) and of the interactive composition (described below) are readily determined by one skilled in the clinical chemistry art.

The compositions of this invention can be used to determine an analyte which is capable of producing NADH, NADPH or FADH by a reaction or series of reactions by including an appropriate interactive composition in such compositions which produces the reductant. Analytes which can be determined in this manner include, but are not limited to, oxidoreductases, such as lactate dehydrogenase, pyruvate dehydrogenase, glucose-6-phosphate dehydrogenase, etc.; oxidases, such as glucose oxidase, lactate oxidase, α-glycerophosphate oxidase, etc.; transferases, such as alanine aminotransferase, aspartate aminotransferase, etc.; hydrolases, such as lipase, etc. and others known to one skilled in the clinical chemistry art. The composition of this invention can also be used in competitive binding assays for determining immunologically reactive substances, which include drugs, such as theophylline, phenobarbitol, diphenylhydantoin and digoxin, and antigens, antibodies, and other immunological substances. The invention is particularly useful for the determination of enzymes which can be used as labels in immunoassays.

Although any aqueous fluid can be analyzed, this invention is especially useful for biological fluids, such as urine, cerebral spinal fluid, blood and the like as well as stool secretions and suspensions of human and animal tissue. This method is especially useful for detection of urinary tract infections. A pretreatment step to remove interferences or to concentrate cells prior to the assay may be desirable. This pretreatment step can be accomplished by a filtration, filtration-wash, centrifugation, centrifugation-wash procedure, etc.

This invention is adaptable to both solution and dry element assays. In a solution assay, a solution generally of the cobalt(III) complex, ETA (if used), metallizable dye, nutrient, if required, and interactive composition (if included) is physically contacted and mixed with a liquid test sample in a suitable container (e.g. test tube, petri dish, microtiter plate, beaker, cuvette, etc.). The resulting solution can be incubated, if desired, for a suitable time at a suitable temperature. The sample is then evaluated by measuring the amount of cobalt(III)-dye complex formed. The amount of colored complex detected can be correlated to the amount of reductant (e.g. NADH or NADPH) either initially present in the sample, or produced as a result of the presence of an analyte. Such an evaluation can be done visually or with suitable colorimetric detection equipment and procedures.

Alternatively, the composition and method of this invention can be utilized in a dry analytical element which comprises an absorbent carrier material (e.g. a thin sheet of a self-supporting absorbent or bibulous material, such as filter paper or paper test strips) and the components of the composition described above. Such elements can also contain an interactive composition for the analyte. These elements are known in the art as test strips, diagnostic elements, dip sticks, diagnostic agents and the like.

In some embodiments of the test strips of the invention, it is desirable to separate the components of the reagent composition so as to prevent interaction and prolong shelf life. For example, the cobalt(III) complex can be coated on one side of the support and the metallizable dye and other reagents can be coated on the other side of the support. In other embodiments, the reagents can be separated by forming patterns of the reagents such as by printing. Reference is made to U.S. Pat. Nos. 3,926,732 issued Dec. 16, 1975; 4,046,513 issued Sep. 6, 1977; and 4,215,995 issued Aug. 5, 1980.

Test strips are often used as a convenient way to carry measured amounts of reagent to the test solution in a solution assay. The test strip is placed into a solution that might already contain the analyte to be measured. The reagents dissolve from the test strip into the solution so as to form the reaction solution. In preferred embodiments of the test strips of the present invention, the reagents are carried in a water soluble binder. When the test strip is immersed into the solution, the binder dissolves releasing the reagents. For reasons not understood, this mode of delivery provides improved sensitivity in comparison to the use of freshly made solutions of the reagents. Useful water soluble polymers include N-vinylpyrrolidone polymers such as poly(N-vinyl-2-pyrrolidone) homopolymer as well as copolymers, e.g. copolymers with acrylamide such as poly(acrylamide-co-N-vinyl-2-pyrrolidone) 90:10 by weight.

When employed in dry analytical elements, the composition components can be incorporated into the absorbent carrier material by imbibition, impregnation, coating or another suitable technique. Useful absorbent carrier materials are insoluble and maintain their structural integrity when exposed to water or physiological fluids such as urine or serum. Useful absorbent carrier materials can be prepared from paper, porous particulate structures, porous polymers, cellulose, wood, glass fiber, woven and nonwoven fabrics (synthetic and non-synthetic) and the like. A useful dry analytical element is made by imbibing a solution of the composition into the material and drying. Details for making such elements are well known in the art, as exemplified in U.S. Pat. Nos. 3,092,465 (issued Jun. 4, 1963 to Adams et al) 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued Jun. 2, 1981 to Kondo et al), and U.K. Patent 2,052,057 (published Jan. 21, 1981).

Preferably, the dry analytical elements of this invention have at least one porous spreading zone as the carrier material. This zone, alone or with other zones, can be self-supporting (i.e. composed of a material rigid enough to maintain its integrity), but preferably it is carried on a separate supporting substrate (commonly called a support). Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyesters [e.g. poly(ethylene terephthalate)], polycarbonates, cellulose esters (e.g. cellulose acetate), etc.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sep. 29, 1981 to Kitajima et al). Alternatively, and preferably, the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and 4,258,001 (issued Mar. 24, 1981 to Pierce et al). Other useful spreading zone materials are described in W. German OLS 3,150,102 (published Jul. 29, 1982) and Japanese Patent Publication 57(1982)-101760 (published Jun. 24, 1982), both assigned to Konishiroku Photo. It is desirable that the spreading zone be isotropically porous, meaning that the porosity is the same in each direction in the zone as created by interconnected spaces or pores between particles, fibers, polymeric strands, etc.

The elements can have more than one zone, e.g. one or more reagent zones, spreading zones, registration zone, mordant zone, radiation-blocking (or filter) zone, subbing zone, barrier zone, buffer zone, etc. The zones are generally in fluid contact with each other meaning that fluids, reagents and reaction products can pass between superposed regions of adjacent zones unless the zones are designed to inhibit the passing of certain materials. Preferably, the zones are separately coated layers, although two or more zones can be a single layer, or a zone can contain two or more separate layers. Besides the references noted above, suitable element formats and components are described, for example, in U.S. Pat. Nos. 4,042,335 (issued Aug. 16, 1977 to Clement). 4,132,528 (issued Jan. 2, 1979 to Eikenberry et al), and 4,144,306 (issued Mar. 13, 1979 to Figueras).

The components of the compositions of this invention, i.e. cobalt(III) complex, ETA (if present), metallizable dye, nutrient, if required, interactive composition (if present), and other optional components can be incorporated in any of the zones of the elements that would be suitable for the particular analysis. For example, a mordant may be useful in the zone containing the resulting dye to reduce its tendency to wander. The location of individual components is within the skill of a worker in the clinical chemistry art.

In the elements of this invention, the amount of the cobalt(III) complex can be varied widely, but it is generally present in a coverage of up to about 50, and preferably from about 0.2 to about 20 g/m$^2$. The ETA (if used) is present in a coverage of up to about 10, and preferably from about 0.01 to about 1.0 g/m$^2$. The metallizable dye is generally present in an amount of up to about 8, and preferably from about 0.01 to about 2 g/m$^2$. When NADH and NADPH are the reductants being determined in response to an analyte, the corresponding oxidized forms, NAD or NADP, are generally present in the element in an amount of up to about 8 g/m$^2$. A variety of other desirable, but optional reagents and addenda can be present in the element in amounts known to one skilled in the art. Such materials include surfactants, buffers, substrates, binders, pigments, activators, mordants, subbing materials, reagents for the interactive compositions, etc.

One embodiment of this invention is a multilayer dry analytical element for determining an analyte. This element comprises a support having thereon, in order and in fluid contact, a registration layer containing a hydrophilic binder material (natural or synthetic), such as gelatin or polyacrylamide, and a porous spreading layer. The element also comprises: 1) a cobalt(III) complex, 2) a metallizable dye, 3) preferably an ETA, and, if necessary, 4) a nutrient, and, if necessary, 5) an interactive composition that produces NADH, NADPH or FADH upon interaction with the analyte. This element can also include a mordant layer between the registration and spreading layers. This layer can contain one or more polymeric mordants, such as those described in U.S. Pat. No. 4,166,093 (issued Aug. 28, 1979 to Smith-Lewis et al).

A variety of different elements, depending on the method of assay, can be prepared in accordance with the present invention. Elements can be configured in a variety of forms, including elongated tapes of any desired width, sheets, slides or chips.

The assay of this invention can be manual or automated. In using the dry elements, the determination is made by taking the element from a supply roll, chip packet or other source and physically contacting it with a sample (e.g. 1–200 μl) of the aqueous liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

Determination of the reductant (e.g. NADH, NADPH) or an analyte is achieved when the cobalt(III) dye complex is formed. This complex can be detected visually or with suitable spectrophotometric means and procedures.

MATERIALS

*Escherichia coli* (*E. coli*) cells were obtained from American Type Culture Collection, Rockville, MD., ATCC No. 25922.

Brain heart infusion medium, sheep blood agar, and MacConkey's medium were obtained from Difco Labs, Detroit, MI.

Triton X-100 TM was obtained from Rohm and Haas, Philadelphia, PA.

Trimethyl-1,4-benzoquinone (TMBQ) was prepared by a standard oxidation of the corresponding hydroquinone, which was obtained from Aldrich Chemical Co., Milwaukee, WI.

2,3-Dimethoxy-5-methyl-1,4-benzoquinone was obtained from Fluka AG Chemical Fabrik, Buchs, Switzerland. 4,5-Dimethoxy-1,2-benzoquinone was prepared by a known preparation (Y. Itoh et al, *Bull. Chem. Soc. Japan*, 52, 2169:1979). Other reagents were obtained from Eastman Kodak Company.

METHODS

Preparation of *E. coli* Cells:

Cells were grown in brain heart infusion medium at 37° C. in static culture and transferred daily. Forty milliliters of cells that were grown overnight were harvested by centrifugation and resuspended in 10 mL of 0.05M potassium phosphate buffer (hereinafter "KP" buffer) (pH 7.5). A stock solution was prepared with an approximate cell concentration of $5 \times 10^8$ cells/mL as determined by reading the optical density at 620 nm at 37° C. An optical density of 0.833 corresponds to an approximate cell density of $5 \times 10^8$ cells/mL.

E$^o$ Measurement

Potentials (E$^o$) were obtained from cyclic voltammograms or polarograms of the various cobalt(III) amine complexes and the cobalt(II) complexes of the metallizable dyes. Potential measurements were made using a PAR Model 174 polarographic analyzer (Princeton Applied Research, Princeton, NJ) by standard techniques (see e.g. Sawyer and Roberts, Jr., *Experimental Electrochemistry for Chemists*, John Wiley and Sons, N.Y., 1974).

Cobalt(II) dye complexes were prepared in situ by anaerobically mixing in an electrochemical cell cobaltous chloride and the metallizable dye (one equivalent of each) in deoxygenated sodium phosphate buffer (pH 7.0, $\mu=0.1$). Final concentration of each component was $2.5 \times 10^{-4}$M. Cobalt(III) amine complexes were added as solid directly to the cell. Final concentration was $5.0 \times 10^{-4}$M. Potential values are reported versus the normal hydrogen electrode (NHE).

Rate Constant Measurement

Rate constants for various cobalt(III) complexes with the same metallizable dye, D-2, were determined as follows:

Absorbance was read at a wavelength at which the Co(III)-dye complex has high absorbance and the unmetallized dye has low absorbance, i.e., 580–680 nm, using a spectrophotometer at 25° C. The following stock solutions were used:

(1) Buffer (pH 7, $\mu=0.1$), by diluting a mixture of 1M potassium dihydrogen phosphate (22.6 mL) and 1M potassium hydrogen phosphate (26.8 mL) to 1 liter, (2)

$CoCl_2 \cdot 6H_2O$ ($1 \times 10^{-2}M - 1 \times 10^{-6}M$), (3) Cobalt(III) complex in buffer ($6 \times 10^{-3}M$), and (4) Metallizable dye in buffer ($1 \times 10^{-2}M$).

Solutions were added to cuvettes in the following order: buffer (2.40 mL), dye (0.03 mL, final concentration $1 \times 10^{-4}M$), Co(III) complex (0.50 mL, final concentration $1 \times 10^{-3}M$) and cobaltous chloride (0.07 mL, final concentration range $10^{-5}$–$10^{-8}M$). A control cuvette contained an additional 0.07 mL of buffer and no cobaltous chloride, and the rate of absorbance change for the control was subtracted from the rate of absorbance change for the test samples. The optical densities were recorded as a function of time and plotted. From the slope of this plot the rate constant of dye formation was calculated.

Rate constants of various metallizable dyes using the same cobalt(III) complex, $[Coen_2(2,2'\text{-bipyridine})]Cl_3$, were determined in the same manner.

Typical Preparation of a Cobalt(III) Complex

Bis(ethylenediamine)2,2'-bipyrimidinecobalt(III) Chloride, C-6

Trans-dichlorobis(ethylenediamine)cobalt(III) chloride (prepared by the method of J. C. Bailar, Jr., "Inorganic Syntheses", Vol. II, 223:1946), 2.85 g (10 mmol) and 2,2'-bipyrimidine (Alfa Products, Danvers, Mass), 1.58 g (10 mmol) were mixed together in 13 mL of water and heated at 100° C. for 50 minutes. The solution was filtered and while warming and stirring the filtrate, ethanol (26 mL) was slowly added and the solution was allowed to cool in a dark area. The large orange crystals of the complex were collected by filtration, washed with 1:2 water:ethanol, then with ethanol and dried by suction. Yield: 3.67 g (83%). The product was recrystallized from 10 mL warm water to which 20 mL of ethanol was slowly added, yielding 3.03 g. A second recrystallization from 8 mL warm water and 16 mL ethanol afforded pure product. The desired compound was confirmed by nuclear magnetic resonance spectroscopy and elemental analysis.

TYPICAL DYE PREPARATION

-2-(3'-Methyl-2'-pyridylazo)-1-Naphthol-4-Sulfonic Acid Ammonium Salt

Step 1: Preparation of 2-Bromo-3-Methylpyridine

This intermediate was prepared by the method of L. C. Craig, *J. Amer. Chem. Soc.*, 56, 231:1934).

Step 2: Preparation of 2-Hydrazino-3-Methylpyridine

A 1 L, 3-neck flask, equipped with stirrer, reflux condenser and outlet to a positive pressure of nitrogen was purged with nitrogen and charged with 130 g of 2-bromo-3-methylpyridine and 350 mL of 95% hydrazine. The mixture was stirred under reflux for 7 hours and then allowed to cool to room temperature slowly. A large amount of the product crystallized in the flask. It was collected, washed with a little ice-cold water and dried by suction. Recrystallization from hot cyclohexane-toluene afforded 52 g of product, mp 123°–124°. The filtrate from the reaction mixture was treated with 60 mL of 50% sodium hydroxide, then concentrated on a rotary evaporator to give an oily residue. This was extracted with five 200 mL portions of hot toluene. The combined extracts were dried and concentrated to an oil, which was crystallized from cyclohexane-toluene to yield more product.

Step 3: Preparation of 2-(3'-Methyl-2'-pyridylazo)-1-Naphthol-4-Suflonic Acid Ammonium Salt 1,2-Naphthoquinone-4-sulfonic acid sodium salt, 10.4 g, was dissolved in 225 mL water and 125 mL of concentrated hydrochloric acid and the solution was filtered. In a separate vessel, 2-hydrazino-3-methylpyridine, 4.92 g, was dissolved in 50 mL water and sufficient hydrochloric acid to aid in dissolving the compound. This solution was filtered and added dropwise to the stirred solution of the quinone. The dye forms almost immediately. The mixture was stirred for 30 minutes after the addition. The product was collected, washed with 0.1N hydrochloric acid, then water and then dried by suction. The product was suspended in acetone, filtered again and washed with acetone, then ether and then dried by suction. Yield 10.4 g of red dye. The dye is suspended in water (100–200 mL) and sufficient 1:1 water, concentrated ammonium hydroxide was added to dissolve the dye. The solution was filtered and the filtrate evaporated on a rotary evaporator to a volume of 100–200 mL. While stirring and warming the solution, acetone was slowly added until the dye began to crystallize (total volume may be 2 liters). The mixture was allowed to cool at room temperature, then chilled in ice. The crystals of the ammonium salt of the dye were collected, washed with acetone and dried by suction. Yield 7.3 g. The desired structure was confirmed by infrared and nuclear magnetic resonance spectroscopy and elemental analysis.

EXAMPLE 1

Detection of NADH Using Dye D-1 and Complex C-2

A test solution was prepared in a 1 cm path length cuvette from 0.1 mL of dye D-1 solution ($7.5 \times 10^{-3}M$ in KP buffer, pH 7.5), 0.5 mL C-2 solution ($5.9 \times 10^{-3}M$ in KP buffer), 0.1 mL NADH solution ($2.0 \times 10^{-5}M$ in water) and 5.1 mL of 0.05M KP buffer. A control solution contained all of the above components except NADH. These solutions were incubated at 37° C. and the transmission densities were read in a Cary spectrophotometer at 610 nm at 2 minutes and at 36 minutes. The change in density for the control was 0.0050 absorbance units; the difference in density for the test solution was 0.0513 absorbance units. The concentration of NADH detected was $3.4 \times 10^{-7}M$.

EXAMPLE 2

Detection of *E. coli* Using Dye D-1 and Cobalt(III) Complex C-2

Stock solutions of the following components were prepared: KP buffer, 0.05M, pH 7.5; dye D-1, $7.5 \times 10^{-3}M$ in buffer; C-2, $5.9 \times 10^{-3}M$ in buffer; glucose, 0.28M in water; TMBQ, 0.01M in methanol and *E. coli* cells, $5 \times 10^5$ cells/mL in buffer.

Test solutions were prepared from buffer, D-1, C-2, glucose, TMBQ, and *E. coli*. Control solutions were prepared as follows: control 1 contained all of the above components, except cells; control 2 contained all of the components, except TMBQ; and control 3 contained all components, except TMBQ and cells. Compositions of the test and control solutions are listed in Table VII.

The solutions were incubated at 37° C., and the optical densities were measured in a 1 cm path length cuvette in a spectrophotometer at 610 nm at 2 minutes, 32 minutes, and 64 minutes. The density differences ($\Delta D_T$) are listed in Table VII. The data indicate that E. coli cells can be detected at concentrations as low as $1 \times 10^4$ cells/mL after 60 minutes (Test 3) and an ETA is required for best sensitivity (Control 2).

TABLE VII

Detection of E. coli Using D-1 and C-2

| | Buffer (mL) | Complex C-2 (mL) | Dye 1 (mL) | Glucose (mL) | TMBQ (mL) | E. coli Final Concentration (cells/mL) | $\Delta D_T$ 30 min | $\Delta D_T$ 62 min |
|---|---|---|---|---|---|---|---|---|
| Control 1 | 5.0 | 0.5 | 0.1 | 0.1 | 0.1 | — | 0.0114 | 0.0312 |
| Control 2 | 5.1 | 0.5 | 0.1 | 0.1 | — | $4.5 \times 10^6$ | 0.0058 | — |
| Control 3 | 5.1 | 0.5 | 0.1 | 0.1 | — | — | 0.0034 | — |
| Test 1 | 5.0 | 0.5 | 0.1 | 0.1 | 0.1 | $1 \times 10^5$ | 0.0437 | 0.1718 |
| Test 2 | 5.0 | 0.5 | 0.1 | 0.1 | 0.1 | $5 \times 10^4$ | 0.0253 | 0.0992 |
| Test 3 | 5.0 | 0.5 | 0.1 | 0.1 | 0.1 | $1 \times 10^4$ | 0.0156 | 0.0517 |

EXAMPLE 3

Detection of E. coli Using Dye (D-1) and Cobalt(III) Complex (C-3)

Stock solutions of the following components were prepared: 0.05M KP buffer (pH 7.8); glucose, 10% (w/v) solution in water; D-1, $7.53 \times 10^{-3}$M in buffer; TMBQ, 1.5 mg/mL in methanol; E. coli cells in buffer, $5 \times 10^8$ cells/mL; C-3, $5.94 \times 10^{-3}$M in buffer.

In a 1 cm path length cuvette, the following solutions were mixed: 2.5 mL buffer, 25 µL glucose solution, 50 µL of D-1, 25 µL of TMBQ solution, 500 µL of C-3 and 250 µL of E. coli cells. A control cuvette contained all the components except cells (buffer was added to make the volumes equivalent). The cuvettes were placed in spectrophotometer at 37° C., and the optical densities were read at 2 minutes and 12 minutes at 610 nm. Results are shown in Table VIII for two different samples of C-3.

TABLE VIII

Detection of E. coli Using D-1 and C-3

| | E. coli (cells/mL) | $\Delta$OD (10 min) 610 nm | $\Delta$OD (control subtracted) |
|---|---|---|---|
| Control | 0 | 0.076 | |
| Sample 1 | $4 \times 10^6$ | 0.524 | 0.448 |
| Control | 0 | 0.306 | |
| Sample 2 | $4 \times 10^6$ | 0.866 | 0.560 |

EXAMPLE 4

Detection of E. coli Using Dye D-1 and Cobalt(III) Complexes C-4 and C-5

Example 3 was repeated using cobalt complexes C-4 and C-5 instead of C-3. Optical densities were read at 2 minutes and at 30 minutes. Results are listed in Table IX.

TABLE IX

Detection of E. coli Using Dye D-1 and Cobalt (III) Complexes C-4 and C-5

| | E. coli (cells/mL) | $\Delta$OD (28 min) 610 nm | $\Delta$OD (control subtracted) |
|---|---|---|---|
| Control | 0 | 0.136 | |
| Complex 4 | $4 \times 10^7$ | 0.262 | 0.126 |
| Control | 0 | 0.01 | |
| Complex 5 | $4 \times 10^7$ | 0.215 | 0.205 |

EXAMPLE 5

Detection of E. coli Using Various Metallizable Dyes

The following stock solutions were prepared: 0.05M KP buffer pH 7.8; glucose, 10% (w/v) in water; dye, $\approx 8 \times 10^{-3}$M in buffer (actual concentrations in Table); TMBQ, 1.5 mg/mL in methanol; E. coli in buffer, $5 \times 10^7$ cells/mL; cobalt(III) complex C-1, $5.94 \times 10^{-3}$M in buffer.

Solutions (0.05 mL) of each of the various dyes were mixed in 3 mL cuvettes with the following solutions: 2.34 mL buffer; 0.025 mL glucose solution; 0.5 mL C-1 solution; 0.025 mL TMBQ solution and 0.06 mL E. coli. A control contained all the above components, except cells. The cuvettes were incubated at 37° C., and the optical densities were measured at 610 nm in a spectrophotometer at time 0 and at 30 minutes. Results, shown in Table X, indicate that Dye 5 is the most sensitive dye of the group.

TABLE X

Detection of E. coli Using Various Metallizable Dyes

| Molar Dye Concentration | | E. coli Final Conc. (cells/mL) | $\Delta$OD (30 min) 610 nm | $\Delta$OD (control subtracted) |
|---|---|---|---|---|
| D-1 | Control | 0 | 0.052 | |
| ($7.53 \times 10^{-3}$) | Test | $1 \times 10^6$ | 0.222 | 0.170 |
| D-2 | Control | 0 | 0.058 | |
| ($7.5 \times 10^{-3}$) | Test | $1 \times 10^6$ | 0.299 | 0.241 |
| D-3 | Control | 0 | 0.060 | |
| ($7.5 \times 10^{-3}$) | Test | $1 \times 10^6$ | 1.010 | 0.950 |
| D-4 | Control | 0 | 0.093 | |
| ($8.9 \times 10^{-3}$) | Test | $1 \times 10^6$ | 0.366 | 0.273 |
| D-5 | Control | 0 | 0.135 | |
| ($9.2 \times 10^{-3}$) | Test | $1 \times 10^6$ | 1.360 | 1.225 |

EXAMPLE 6

Detection of Organisms in Urine Samples (Comparison of Cobalt Chemistry and Commercial Systems)

This example compares the use of cobalt chemistry, wherein reagents are coated in a water-soluble polymer and reconstituted, and two commercial systems for the detection of organisms in urine samples.

Seventy-three urine samples were obtained from local hospitals. Plate counts were obtained for each sample by growth on Sheep Blood Agar (Baltimore Biological Labs, Cockeysville, MD) at 37° C. for 72 hours in 5% carbon dioxide, or on Saboroud Dextrose Agar (Difco Labs, Detroit, MI) at 30° for 72 hours for yeast.

Commercial systems compared were: CHEM-STRIP TM 9 (leucocyte esterase and nitrite UTI screen from Bio-Dynamics-Boehringer-Mannheim, Indianapolis, IN) and BAC-T-SCREEN TM with DYNA- DEPTH ™ Test Card Reader (Safrain O dye stain UTI screen from Marion Scientific, Kansas City, MO).

Cobalt Chemistry Coatings

Two coatings on poly(ethyleneterephthalate) film support were made of the following: coating (1) contained poly(acrylamide-co-N-vinyl-2-pyrrolidone) 0.9:1; 1.08 g/m² and Zonyl FSN surfactant, 0.22 g/m², filtered through a 0.2μ MILLIPORE ™ filter (Millipore Corp., Bedford, MA), cobalt complex C-1, 16.14 g/m² and glucose 2.15 g/m². Coating (2) contained poly(acrylamide-co-N-vinyl-2-pyrrolidone) and Zonyl FSN, as above, and dye D-6, 1.08 g/m².

These coatings were then cut into 1 cm² chips and reconstituted by adding them to solutions containing potassium phosphate buffer (pH 6.8) and 25 μL ETA 4,5-dimethoxy-1,2-benzoquinone (1.62 mg/mL methanol) (total volume 3 mL).

Tests were run in plastic cells containing a filter membrane ULTIPOR N66 ™ nylon filter, Pall Trinity Micro Corp., Cortland, NY) with absorbent cotton underneath the filter and a vacuum port to aid in filtration. Optical density measurements were made at one-minute intervals for 30 minutes at 610 nm and 36° C. in a modified conventional spectrophotometer.

The following solutions were added to the cells: first, 0.5 mL of the urine sample, then 0.5 mL solution of 0.005M ferric ethylenediaminetetraacetic acid (Fe EDTA) and 1% Triton X-100 surfactant, then 0.5 mL buffer (pH 6.8), each solution was filtered by vacuum, and lastly 0.5 mL of a solution containing the reconstituted cobalt reagents. The tops of the wells were heat sealed with PARAFILM ™ (American Can Co., Greenwich, CT) and the optical densities were read. Control solutions containing buffer were also read.

Results are expressed as percent sensitivity, specificity and predictive values* and are shown in the tables.
*For a further explanation of these terms see Beyond Normality: The Predictive Value and Efficiency of Medical Diagnoses, R. S. Galen and S. R. Gambino, John Wiley & Sons, N.Y., 1975.

Sensitivity is a measure of the percent positivity in the assay and is defined as:

$$\frac{true\ positives\ (TP)}{true\ positives\ (TP) + false\ negatives\ (FN)} \times 100.$$

Specificity is a measure of the percent negativity in the assay and is defined as:

$$\frac{true\ negatives\ (TN)}{true\ negatives\ (TN) + false\ positives\ (FP)} \times 100.$$

Predictive value of a positive result is a measure of percent of positive results that are true positives and is defined as:

$$\frac{TP}{TP + FP} \times 100.$$

Predictive value of a negative result is a measure of percent of negative results that are true negatives and is defined as:

$$\frac{TN}{TN + FN} \times 100.$$

Comparison of Cobalt Chemistry with BAC-T-SCREEN ™ and CHEMSTRIP ™ for Detection of Organisms in Urine.

TABLE XI

| | (1 × 10⁵ organisms/mL)[1] | | |
|---|---|---|---|
| | Cobalt Screen | BAC-T-SCREEN ™ | CHEMSTRIP ™ |
| Sensitivity | 100% | 100% | 88.9% |
| Specificity | 100% | 40.4% | 78.4% |
| Positive Pred. Value | 100% | 38.0% | 59.2% |
| Negative Pred. Value | 100% | 100% | 95.2% |

TABLE XII

| | (1 × 10⁴ organisms/mL)[2] | | |
|---|---|---|---|
| | Cobalt Screen | BAC-T-SCREEN ™ | CHEMSTRIP ™ |
| Sensitivity | 87.0% | 91.3% | 77.3% |
| Specificity | 91.7% | 39.6% | 78.7% |
| Positive Pred. Value | 83.3% | 42.0% | 63.0% |
| Negative Pred. Value | 93.6% | 90.5% | 88.1% |

[1] Positive culture is defined as ≥ 1 × 10⁵ organisms/mL. Positive cobalt response = 0.60 ΔOD at 610 nm (30 min.).
[2] Positive culture is defined as ≥ 1 × 10⁴ organisms/mL. Positive cobalt response = 0.30 ΔOD at 610 nm (30 min.).

EXAMPLE 7

Determination of *E. coli* Using Dye D-20 and Complex C-1

Stock Solutions:
1) Dye 36.5 mg/10 mL of 0.05M KPB, pH 7.8,
2) Co(III) complex 41.4 mg/10 mL KPB, pH 7.8,
3) *E. coli* cells in 0.05M KPB, pH 7.5,
4) ETA-2,3-dimethoxy-5-methyl-1,4-benzoquinone 1.82 mg/ml of methanol and
5) glucose (10% solution in water).

Distilled water and buffer were filtered through 0.2μ MILLIPORE ™ filter. Solutions were added to cuvettes in the following order: buffer (2.34 mL), glucose (25 μL), dye (50 μL), cobalt complex (500 μL), ETA (25 μL), and cells (60 μL). Final cell concentration was 1 × 10⁵ cell/mL. A control contained no cells, but additional buffer was added to make volume equal to test volume (3 ml). The optical densities were measured at 670 nm at 37° C. when solutions were first mixed and after 20 minutes for both control and test solutions. The density difference between control and test solutions was 0.142 absorbance units.

EXAMPLE 8

Determination of White Blood Cells

This example illustrates the use of cobalt(III) chemistry of the invention to determine white blood cells.
Stock solutions:
1) phosphate buffered saline (PBS), 8.5 g sodium chloride in 0.1M potassium phosphate buffer, pH 7.5,
2) Dye D-3 28.4 mg/10 mL 0.05M KPB, pH 7.8,
3) Cobalt(III) complex C-6, 28 mg/10 mL KPB,
4) ETA-(2,3-dimethoxy-5-methyl-1,4-benzoquinone) 1.82 mg/mL methanol,
5) Glucose (10% in water),
6) Dextran (Sigma Chem. Co., St. Louis, MO), 6 g/100 mL water and
7) Lysing solution: 0.83 g ammonium chloride, 0.1 g potassium bicarbonate and 0.03 g (ethylenedinitrilo)tetraacetic acid disodium salt in 100 mL of water, pH 7.2.

Preparation of white blood cells: Blood samples (8.5 mL) were collected in sterile vacutainers containing 1.5 mL acid citrate dextrose. Dextran solution (1.5–2.0 mL) was added and the tubes were mixed by inversion and allowed to set for about 1.5 hours. The plasma layer was transferred to sterile 15 mL centrifuge tubes, the tubes were filled halfway with PBS solution and centrifuged at 10,000 rpm for 10 minutes, and the solutions were then decanted. The cell pellet was resuspended in 10 mL of the lysing solution and the tubes were allowed to set until the solution cleared ($\simeq$5 minutes). The tubes were again centrifuged for 10 minutes, decanted, the cell pellet was resuspended in PBS, centrifuged, decanted and resuspended in about ½ mL PBS solution, and the cells were counted.

Stock solutions were added to cuvettes in the following order: buffer (2.34 mL), glucose (25 μL), dye (50 μL), cobalt complex (500 μL), ETA (25 μL) and white blood cells (60 μL), at concentrations listed in the table. A background control did not contain any cells, but additional buffer was added to make the volume equal to the test volume (3 mL). Solutions were mixed and the optical densities were read at 610 nm at 37° C. when the cells were first added and after 4 minutes. Data are shown in Table XIII.

TABLE XIII

| Cell Concentration (cells/mL) | $\Delta$OD/4 minutes/610 nm |
| --- | --- |
| Control (no cells) | 0.011 |
| $1.5 \times 10^3$ | 0.311 |
| $1.5 \times 10^4$ | 0.427 |
| $1.5 \times 10^5$ | 1.381 |

EXAMPLE 9

Determination of G-6-PDH

This example illustrates the use of a cobalt composition of the invention to assay for the enzyme glucose-6-phosphate dehydrogenase (G-6-PDH).

Reagents and solutions used:

| | | |
| --- | --- | --- |
| 1) | Potassium phosphate buffer, 0.1M, pH 7.0 | 1.375 mL |
| 2) | Magnesium chloride, 0.1M in water | 0.200 |
| 3) | Glucose-6-phosphate, 0.029M in water | 0.100 |
| 4) | Nicotinamide adenine dinucleotide phosphate (NADP), 0.011M in water | 0.100 |
| 5) | TMBQ, 1.5 mg/mL methanol | 0.025 |
| 6) | Dye D-6, 30.5 mg/10 mL buffer | 0.050 |
| 7) | Diaphorase, 10 mg/mL water | |
| 8) | Cobalt (III) complex C-1 28 mg/10 mL buffer | 1.000 |
| 9) | G-6-PDH, from yeast | 0.020 |

Diaphorase was obtained from Sigma Chem. Co., St. Louis, MO. G-6-PDH was obtained from Boehringer Mannheim, Indianapolis, IN.

Test solutions were mixed in the above order at 25° C. A control solution was also prepared without the enzyme G-6-PDH. Absorbance was read at 610 nm in a spectrophotometer. The results are listed in Table XIV as the time required to reach an absorbance change of 0.5 units after the enzyme was first added to the solutions.

TABLE XIV

| Final Enzyme Concentration (molar) | Time (min.) to reach $\Delta$A of 0.5 units/610 nm/25° C. |
| --- | --- |
| 0 (control) | 104 |
| $1.7 \times 10^{-13}$ | 83 |
| $3.4 \times 10^{-13}$ | 69 |
| $8.4 \times 10^{-13}$ | 49 |
| $1.7 \times 10^{-12}$ | 34 |

EXAMPLE 10

Element for the Determination of E. coli

This example illustrates the use of cobalt(III) chemistry of the invention in an element format to determine E. coli.

The following reagents were coated onto subbed polyethylene terephthalate film support at pH 3.5: poly(acrylamide-co-N-vinyl-2-pyrrolidone) 9:1, filtered thru a 0.2μ Millipore filter (0.1 g/m² to 12 g m², preferred 1 g/m²), Zonyl FSN surfactant (Du Pont Co., Wilmington, DE), filtered thru a 0.2μ Millipore TM filter (0.01 g/m² to 2 g/m², preferred 0.2 g/m²), dye D-7 (0.01 to 8 g/m², preferred 1 g/m²), glucose (0.2 g/m² to 20 g/m², preferred 2 g/m²) and 2,3-dimethoxy-5-methyl-1,4-benzoquinone (0.01 g/m² to 10 g/m², preferred 0.8 g/m²) and cobalt(III) complex, C-1, (0.2 to 50 g/m², preferred 10.8 g/m²).

SAMPLES

In a dark area, four 1 cm² square chips of the above coatings were tested as follows: three of the chips were spotted with 100 μL of various cell concentrations in phosphate buffer (pH 7), and the fourth was spotted with 100 μL of 0.05M potassium phosphate buffer as the background control. After incubation at 37° C. for 30 minutes, the reflection density was measured at 610 nm in a modified conventional reflectometer. Results, shown in Table XV, indicate that an element of this invention can be used to detect various concentrations of E. coli.

TABLE XV

| E. coli cell concentration | $D_R$, 610 nm background corrected* |
| --- | --- |
| $1 \times 10^5$ | 0.215 |
| $5 \times 10^5$ | 0.217 |
| $1 \times 10^6$ | 0.340 |

*A control without cells was subtracted from the test values.

The invention has been described in detail with particular reference to preferred embodiments thereof, but it will be understood that variations and modifications can be effected within the spirit and scope of the invention.

What is claimed is:

1. A method for the detection of an analyte in an aqueous sample wherein said analyte is either itself a reductant or is capable of producing a reductant comprising the steps of:
   (a) contacting said sample with reagents which effect in the presence of said analyte a sequence of reactions wherein:
      (1) a water soluble cobalt(III) complex is reduced to a water soluble cobalt(II) complex by said reductant,
      (2) the cobalt(II) complex reacts with a water soluble dye to form a cobalt(II)-dye complex and (3) the cobalt(II)-dye complex reacts with the cobalt(III) complex to produce a cobalt(III)-dye complex and the cobalt(II) complex, (b) detecting the cobalt(III)-dye complex and relating said detected complex to said analyte.

2. A method according to claim 1 wherein said analyte is a biological material, or is produced by a biological material.

3. A method according to claim 2 wherein said biological material is a living microorganism.

4. A method according to claim 3 which includes the step of incubating a sample suspected of containing said microorganism in a solution containing a nutrient that is capable of being metabolized by said microorganism.

5. A method according to claim 1 wherein said cobalt(III) complex has a redox potential greater than −350 mV vs. a normal hydrogen electrode.

6. A method according to claim 1 wherein the cobalt(II)-dye complex has a redox potential less than +450 mV vs. a normal hydrogen electrode.

7. A method according to claim 6 wherein said water soluble dye is selected from the group consisting of azonaphthol dyes, azophenol dyes, azobenzoic acid dyes, hydrazone dyes and formazan dyes.

8. A method according to claim 7 wherein said water soluble dye is an azo dye having the formula:

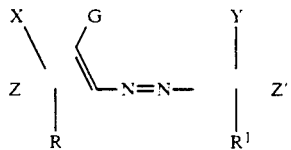

wherein

Z and Z' represent the atoms necessary to complete a substituted or unsubstituted aromatic carbocyclic or heterocyclic nucleus of at least 5-7 atoms, in addition, Z' has, in a position adjacent to the point of attachment of the azo linkage, either (a) a nitrogen atom in the ring of the nucleus which acts as a chelating site, or (b) a carbon atoms in the ring of the nucleus having attached thereto a nitrogen atom which acts as a chelating site;

G is a metal chelating group or a hydrolyzable precursor thereof;

R and $R^1$ independently represent hydrogen, alkyl, alkoxy, halo, hydroxy, amino or sulfamoyl;

X and Y independently represent a group mentioned for R and $R^1$ and at least one of X and Y is a solubilizing group selected from carboxylic acid, sulfate, sulfinic acid, sulfonic acid, alkylsulfonic acid, alkylsulfate or alkylsulfonic acid and alkylsulfate derived from a sulfonamide, or salts thereof.

9. A method according to claim 8 wherein said dye has a solubilizing group in both the X and the Y positions.

10. A method according to claim 8 wherein said dye is selected from the group consisting of 2-[(3-methyl-2-pyridyl)azo]-1-naphthol-4-sulfonic acid, monoammonium salt; 2-[(5-carboxy-2-pyridyl)azo]-1-naphthol-4-sulfonic acid, diammonium salt; and 2-[(3-methyl-5-sulfo-2-pyridyl)azo]-1-naphthol-4-sulfonic acid, diammonium salt.

11. A method according to claim 1 wherein the ligands of said cobalt(III) complex are neutral.

12. A method according to claim 11 wherein said ligands are selected from the group consisting of 1) ammonia, 2) aliphatic amines, 3) aromatic amines, 4) heterocyclic amines and 5) oxygen donors.

13. A method according to claim 1 wherein said cobalt(III) complex is a complex of the formula:

[Co(ethylenediamine)$_2$(2,2'-bipyridine)]Cl$_3$;
[Co(ethylenediamine)$_2$(1,10-phenanthroline)]Cl$_3$;
[Co(ethylenediamine)$_2$(2,2'-bipyrimidine)]Cl$_3$ and
[Co(ethylenediamine)$_2$(5-nitrophenanthroline)]Cl$_3$.

14. A reagent composition for the detection of an analyte in an aqueous sample wherein said analyte is either itself a reductant or is capable of producing a reductant said composition comprising:

(1) a water soluble cobalt(III) complex which is capable of being reduced to a water soluble cobalt(II) complex by said reductant and, (2) a water soluble dye which is capable of being metallized by said cobalt(II) complex to form a water soluble cobalt(II)-dye complex, wherein said cobalt(II)-dye complex is capable of reacting with said cobalt(III) complex to produce a cobalt(III)-dye complex and the cobalt(II) complex.

15. A composition according to claim 14 further comprising an electron transfer agent.

16. A composition according to claim 15 wherein said electron transfer agent is a quinone.

17. A composition according to claim 16 wherein said electron transfer agent is selected from the group consisting of 2,3,5-trimethyl-1,4-benzoquinone, 2,3-dimethoxy-5-methyl-1,4-benzoquinone and 4,5-dimethoxy-1,2-benzoquinone.

18. A composition according to claim 14 further comprising a nutrient that is capable of being metabolized by a microorganism.

19. A composition according to claim 14 wherein said cobalt(III) complex has a redox potential greater than −350 mV vs. a normal hydrogen electrode.

20. A composition according to claim 14 wherein the cobalt(II)-dye complex has a redox potential less than +450 mV vs. a normal hydrogen electrode.

21. A composition according to claim 20 wherein said water soluble dye is selected from the group consisting of azonaphthol dyes, azophenol dyes, azobenzoic acid dyes, hydrazone dyes and formazan dyes.

22. A composition according to claim 21 wherein said water soluble dye is an azo dye having the formula:

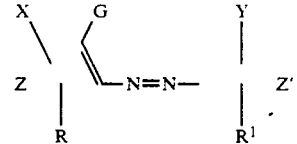

wherein

Z and Z' represent the atoms necessary to complete a substituted or unsubstituted aromatic carbocyclic or heterocyclic nucleus of at least 5-7 atoms, in addition, Z' has, in a position adjacent to the point of attachment of the azo linkage, either (a) a nitrogen atom in the ring of the nucleus which acts as a chelating site, or (b) a carbon atom in the ring of the nucleus having attached thereto a nitrogen atom which acts as a chelating site;

G is a metal chelating group or a hydrolyzable precursor thereof;

R and $R^1$ independently represent hydrogen, alkyl, alkoxy, nitro, halo, hydroxy, amino or sulfonamido;

X and Y independently represent a group mentioned for R and $R^1$ and at least one of X and Y is a solubilizing group selected from carboxylic acid, sulfonic acid, alkylsulfonic acid or alkylsulfonic acid derived from a sulfamoyl group, sulfate, sulfinic acid or salts thereof.

23. A composition according to claim 2 wherein said dye has a solubilizing group in X and the Y positions.

24. A composition according to claim 22 wherein said dye is selected from the group consisting of 2-[(3-methyl-2-pyridyl)azo]-1-naphthol-4-sulfonic acid, monoammonium salt; 2-[(5-carboxy-2-pyridyl)azo]-1-naphthol-4-sulfonic acid, diammonium salt; and 2-[(3-methyl-5-sulfo-2-pyridyl)azo]-1-naphthol-4-sulfonic acid, diammonium salt.

25. A composition according to claim 14 wherein the ligands of said cobalt(III) complex are neutral.

26. A composition according to claim 25 wherein said ligands are selected from the group consisting of 1) ammonia, 2) aliphatic amines, 3) aromatic amines, 4) heterocyclic amines and 5) oxygen donors.

27. A composition according to claim 14 wherein said cobalt(III) complex is a complex of the formula:
[Co(ethylenediamine)$_2$(2,2'-bipyridine)]Cl$_3$;
[Co(ethylenediamine)$_2$(1,10-phenanthroline)]Cl$_3$;
[Co(ethylenediamine)$_2$(2,2'-bipyrimidine)]Cl$_3$ and
[Co(ethylenediamine)$_2$(5-nitrophenanthroline)]Cl$_3$.

28. A dry element comprising an absorbent carrier material containing a composition for the detection of an analyte in an aqueous sample wherein said analyte is either itself a reductant or is capable of producing a reductant said composition comprising:
(1) a water soluble cobalt(III) complex which is capable of being reduced to a water soluble cobalt(II) complex by said reductant and,
(2) a water soluble dye which is capable of being metallized by said cobalt(II) complex to form a water soluble cobalt(II)-dye complex,
wherein said cobalt(II)-dye complex is capable of reacting with said cobalt(III) complex to produce a cobalt(III)-dye complex and the cobalt(II) complex.

29. A dry element containing a composition according to claim 28 further comprising a nutrient.

* * * * *